United States Patent
Lancial

(10) Patent No.: US 7,819,899 B2
(45) Date of Patent: Oct. 26, 2010

(54) INSTRUMENT FOR PEDICLE SCREW ADHESIVE MATERIALS

(75) Inventor: Mike E. Lancial, St. Louis Park, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 379 days.

(21) Appl. No.: 11/324,643

(22) Filed: Jan. 3, 2006

(65) Prior Publication Data

US 2007/0156143 A1 Jul. 5, 2007

(51) Int. Cl.
*A61B 17/70* (2006.01)

(52) U.S. Cl. ...................... 606/246; 606/264

(58) Field of Classification Search .......... 606/61, 606/246, 250–279, 300–331; 411/82, 82.1; 403/399; 439/781, 793
See application file for complete search history.

(56) References Cited

U.S. PATENT DOCUMENTS

| | | | |
|---|---|---|---|
| 5,672,176 A * | 9/1997 | Biedermann et al. | 606/271 |
| 6,050,997 A | 4/2000 | Mullane | |
| 6,113,638 A * | 9/2000 | Williams et al. | 128/898 |
| 6,280,443 B1 | 8/2001 | Gu et al. | |
| 6,488,681 B2 | 12/2002 | Martin et al. | |
| 6,540,749 B2 * | 4/2003 | Schafer et al. | 606/61 |
| 6,565,565 B1 * | 5/2003 | Yuan et al. | 606/61 |
| 6,641,586 B2 * | 11/2003 | Varieur | 606/61 |
| 6,716,214 B1 * | 4/2004 | Jackson | 606/61 |
| 6,752,402 B2 | 6/2004 | Grotendorst et al. | |
| 6,989,254 B2 | 1/2006 | Wei et al. | |
| 2004/0138660 A1 * | 7/2004 | Serhan | 606/61 |
| 2005/0256578 A1 * | 11/2005 | Blatt et al. | 623/17.15 |
| 2006/0025767 A1 * | 2/2006 | Khalili | 606/61 |
| 2006/0241600 A1 * | 10/2006 | Ensign et al. | 606/61 |
| 2006/0276788 A1 * | 12/2006 | Berry et al. | 606/61 |
| 2007/0016193 A1 * | 1/2007 | Ritland | 606/61 |
| 2007/0093820 A1 * | 4/2007 | Freudiger | 606/61 |

* cited by examiner

*Primary Examiner*—Thomas C Barrett
*Assistant Examiner*—Nicholas Woodall
(74) *Attorney, Agent, or Firm*—Crompton, Seager & Tufte, LLC.

(57) ABSTRACT

Spinal stabilization systems and the assembly, interconnection, and use of such systems are described which provide stabilization of vertebrae in the spine. Devices and methods of the invention may be used to attach a bone engaging element such as a fastener to a spinal stabilization element such as a rod or a cord by bonding with a bonding material. A spinal stabilization system of the invention may include a fastener with a connector portion, a spinal stabilization element, and a body. The body encloses a portion of the fastener and a spinal stabilization element to create a cavity. A bonding material may be applied to the cavity to bond a portion of the fastener with a portion of the spinal stabilization element. The system may also include cap to close the cavity.

11 Claims, 7 Drawing Sheets

INSTRUMENT FOR PEDICLE SCREW ADHESIVE MATERIALS

TECHNICAL FIELD

The present invention relates generally to techniques for stabilizing vertebrae by spinal surgery. More particularly, the present invention relates to devices and methods involving components of spinal stabilization systems and the assembly, interconnection, and use of such components to provide a spinal stabilization system for stabilization of vertebrae in the spine.

BACKGROUND

The spinal column is a complex system of bones and connective tissue that protects critical elements of the nervous system. Despite these complexities, the spine is a highly flexible structure, capable of a high degree of curvature and twist through a wide range of motion. Trauma, disease, or developmental irregularities can result in spinal pathologies that limit this range of motion.

Orthopaedic surgeons commonly perform procedures to correct spinal irregularities and restore stability to the spine through stabilization or immobilization of vertebrae within the spine. A stabilization procedure is often performed to alleviate the pain and discomfort that can be caused by a herniated or slipped disc. In such a procedure, the damaged disk is surgically removed from the space between adjacent vertebrae and an implant, such as a bone graft or cage, is then positioned between the adjacent vertebra. The implant promotes fusion of the adjacent vertebra thereby stabilizing the spine. A spinal stabilization system is sometimes used during fusion to stabilize the adjacent vertebra.

One example of a spinal stabilization system is disclosed in U.S. Pat. No. 6,050,997 to Mullane. This system includes spinal constructs having connective structures such as elongated rods that are secured adjacent the portion of the spinal column intended to be immobilized. Bone anchors, such as screws and hooks, are commonly utilized to attach the connective structures to the posterior surfaces of the spinal laminae. These components may provide the necessary stability both in tension and compression to achieve the desired stabilization of a portion of a spine.

Various fastening techniques and devices are used to secure bone anchors to the rod or cord of a spinal stabilization system. For example, in one system, the bone screws have a receiving slot or opening in a head portion of the screw for receiving a rod or cord. To accommodate connection to a rod or cord, many of these bone screws are open-ended at one end and have a yoke with a pair of upstanding arms that can receive the rod in a channel formed between the arms. The bone screws are implanted in predetermined vertebrae of the spine (adjacent vertebra, for example) and a rod or cord is then extended through the slot opening in each bone screw. The bones screws are then connected to the rod or cord by a set screw or nut that engages the rod or cord through or over a wall of the screw head. Tightening the set screw or nut causes the rod or cord to be forced or clamped within the head of the bone screw to provide a holding force that attaches the rod or cord to the bone screw. Applying a pre-specified torque to the screw or nut provides a rigid construct for indefinite duration.

With these mechanical fasteners, the contact area between the fastener and the spinal stabilization element is relatively small. For example, when a set screw is used to force a rod against an inside surface of a yoke of a bone anchor, the contact region between the set screw and the spinal stabilization element is generally limited to the diameter of the set screw. Since the spinal stabilization elements themselves are typically cylindrical, the contact with a flat surface of a set screw is limited to line contact. Shaping the screw contact surface to better correspond to the curved surface of a spinal stabilization element would enhance contact, but limits tightening of a threaded screw. Using a set nut provides only contact with a cylindrical rod or cord at two points. Because of this relatively small contact area, a substantial amount of torque in the range of 100 in. lbs. to 130 in. lbs. is needed in order to provide the required force needed to hold the rod or cord in place. Additionally, anti-torque tools are usually required to assist in tightening the fastener to the required torque. In many cases, one person is needed to torque the fastener while another person provides a countering force with an anti-torque tool.

SUMMARY

The present invention provides components of spinal implant systems and methods of using such components and systems in spinal surgical procedures. In one embodiment, the invention is directed to a system for use in spinal stabilization that includes a fastener having a cradle portion and a connector portion, an elongate spinal stabilization element positioned adjacent the cradle portion at a desired location, a body movably disposed to the cradle portion of the fastener, and a cap connected to the body. In this embodiment, the cradle portion, body, and cap define a cavity that at least partially contacts a surface the spinal stabilization element. The system may also include a bonding material, such as a curable adhesive, disposed within the cavity.

In another embodiment, the invention is directed to a method of spinal stabilization that includes the steps of securing a fastener to a vertebra, the fastener having a cradle portion and a connector portion, positioning a spinal stabilization element adjacent the cradle portion of the fastener at a desired location of the spinal stabilization element, and bonding the cradle portion with the spinal stabilization element.

In yet another embodiment, the invention is directed to a kit for use in spinal stabilization including a plurality of fasteners, each fastener having a cradle portion, an elongate spinal stabilization element positionable adjacent the cradle portions of the plurality of fasteners at different portions along the length of the spinal stabilization element, a plurality of bodies, each movably disposable to at least one fastener, a plurality of caps, each connectable with at least one body, wherein each cradle portion, body and cap define a cavity at least partially surrounding the spinal stabilization element, and a quantity of bonding material able to bond a surface of the cradle portion with a surface of the spinal stabilization element.

BRIEF DESCRIPTION OF THE DRAWINGS

These and other features, aspects, and advantages of the present invention will become better understood with regard to the following description, appended claims, and accompanying drawings where:

DETAILED DESCRIPTION

The present invention provides methods of spine stabilization and apparatuses used in spine stabilization in which a fastener, such as a bone anchor, is secured to a vertebra, a spinal stabilization element is positioned next to the fastener, and the fastener is bonded to the spinal stabilization element. Several benefits are realized by bonding the fasteners to spinal stabilization elements. The need to apply torque to the spinal stabilization system during implantation may be dramatically reduced so that the use of torque and anti-torque tools may be minimized or eliminated altogether. As a result, fewer people and tools may be needed to install the spinal stabilization system of the present invention. Bonding also provides greater contact between connected components such as the fastener and the spinal stabilization element which may result in a more stabilized spine.

Figure 1:
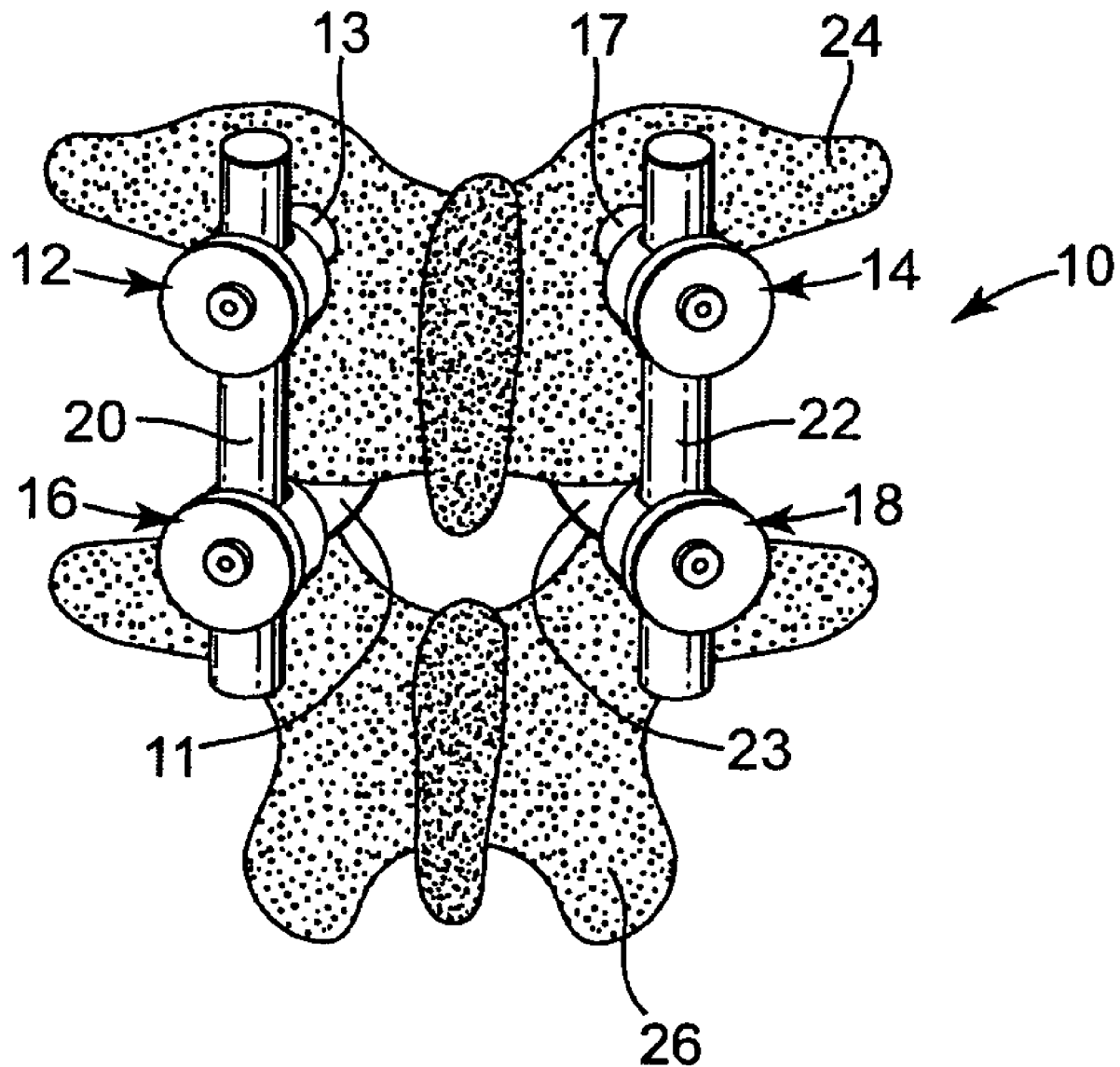
FIG. 1 is perspective view of a spinal stabilization system in accordance with the present invention.

In one embodiment, illustrated in FIG. 1, the spinal stabilization system 10 includes plural attachment devices 12, 14, 16, 18 that are attached to spinal stabilization elements 20, 22 to anchor the spinal stabilization system 10 to vertebrae 24, 26. The attachment devices 12, 14 may include fasteners 13, 17 that are partially implanted into vertebra 24. The fasteners 13, 17 may include bone engaging threaded portions that are used to attach the fasteners 13, 17 to the vertebra 24. Attachment devices 16, 18 secure a second vertebra 26 using fasteners 11, 23 that include a hook portion instead of a threaded portion to connect with vertebra 26. Various types of attachment devices may be used to attach the spinal stabilization system 10 to vertebrae to achieve a desired spinal stabilization.

The attachment devices 12, 14, 16, 18 may be bonded to the spinal stabilization elements 20, 22 with a bonding material. In addition to the bonding material, the attachment devices 12, 14, 16, 18 may optionally be temporarily or permanently connected to the spinal stabilization elements 20, 22 through other mechanical securing components, such as those described below.

Figure 3:
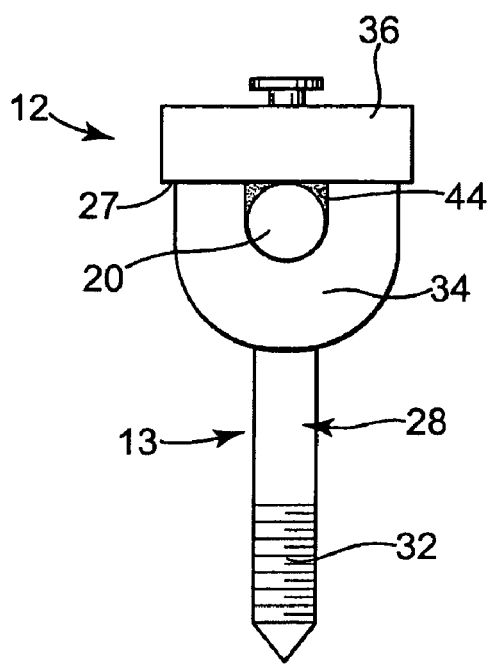
FIG. 3 is a side view of the attachment device of FIG. 2 showing a the fastener connected to a spinal stabilization element, a body, and a cap.
Figure 4:
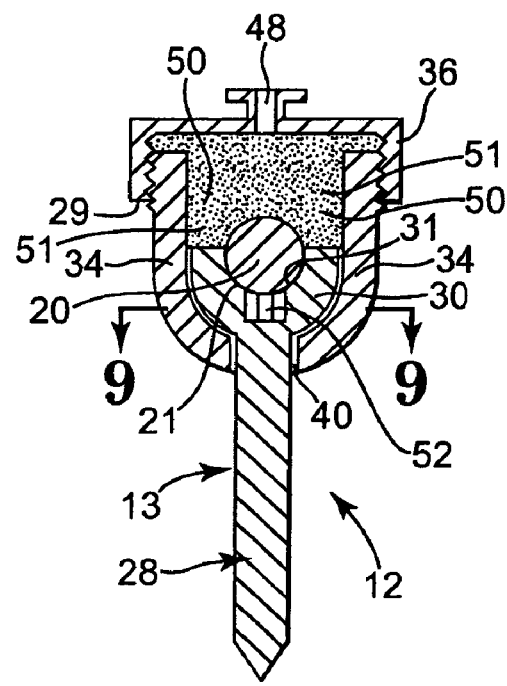
FIG. 4 is a cross-sectional view of the attachment device of FIG. 3.
Figure 9:
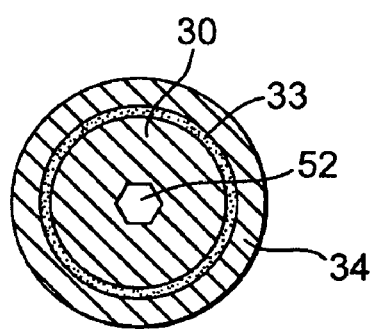
FIG. 9 is an enlarged cross-sectional view of the cradle portion of the fastener and the body of FIG. 4 taken along the line 9-9.

As illustrated in FIGS. 3 and 4, the fastener 13 may include a body 34, cap 36, and cradle portion 30. The body 34, cap 36, and cradle portion 30 of the fastener 13 may substantially define the cavity 50. A bonding material 51 may be applied to the cavity 50 to bond a portion of the attachment device 12 to a portion of a spinal stabilization element 20. Any small clearance 33 between the cradle portion 30 and body 34, as illustrated in FIG. 9, could be included in the cavity 50.

Figure 6:
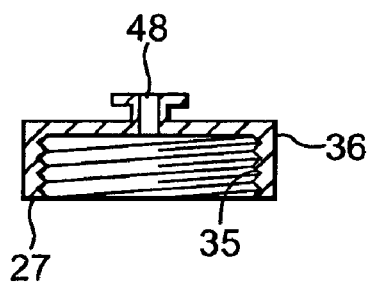
FIG. 6 is a cross-sectional view of the cap of the attachment device of FIGS. 2, 3 and 4.

In one embodiment, a sufficient quantity of bonding material 51 is supplied to fill the volume of the cavity 50. Bonding material 51 may be applied to the cavity 50 in any suitable manner. In one embodiment, the bonding material 51 is injected into the cavity 50 through an inlet 48. The inlet 48 may include any opening or region by which bonding material 51 may be applied to the fastener 13 and spinal stabilization element 20 for at least partially bonding the fastener 13 to the spinal stabilization element 20. The inlet 48 may be located on the cap 36, as shown in FIGS. 4 and 6, or may be located on the body 34, or both on the cap 36 and the body 34. The bonding material 51 may also be supplied into the cavity 50 before the cap 36 is connected to the body 34.

Any leakage of bonding material 51 from around the spinal stabilization element 20, such as through slots 44, may be controlled or cleaned. Any potential leakage sites may be blocked or sealed prior to bonding. For example, the leakage sites may also be blocked by a cover 76, 176, illustrated in FIGS. 7, 8, 17 and 18, and described below.

In another embodiment, a quantity of bonding material 51 is applied directly to a portion of the surface of the cradle portion 30 and a surface of the spinal stabilization element 20. For example, bonding material 51 may be applied to the surface portion 31 of the cradle portion 30 and to the surface portion 21 of the spinal stabilization element 20. These surfaces may then overlap when the spinal stabilization element 20 is positioned adjacent the cradle portion 30. In this embodiment, the bonding material 51 may be applied in any suitable manner such as, for example, spreading the bonding material 51 onto the desired surface portions 21, 31. The surface portions 21, 31 may be treated or modified to improve bonding. For example, these surfaces 21, 31 may be roughened, chemically etched, corona-treated, scored, or otherwise modified to improve bonding or adhesion. One or both of these surface portions 21, 31 may also include recessed regions, grooves, or cavities for containing bonding material 51.

Any suitable bonding material 51 or combination of bonding materials may be used to connect the spinal stabilization element 20 to the fastener 13. Suitable bonding material 51 includes medical grade material so that can be used within the human body. The bonding material 51 may be selected based upon the bonding technique and the needs of the stabilization system. For example, the supplemental stabilization force provided by the other components of the system may be considered in the selection of the bonding material. Suitable bonding material 51 may have sufficient strength to hold or attach the cradle portion 30 to the spinal stabilization element 20 under forces that the spinal fixation system will encounter in use. For example, a spinal stabilization system may experience cyclical loading forces. Therefore, a suitable bonding material 51, along with optional mechanical fastening, may provide a bond that can withstand such forces.

Bonding material 51 may also include materials capable of surrounding or enclosing a portion of a fastener and a spinal stabilization element, such as the cradle portion 30 and spinal stabilization element 20 within cavity 50. For example, bonding materials may include adhesives such as polymer adhesives, cements, metals and metal alloys, synthetic bone, and similar materials. The bonding material 51 may be a flowable material, such as a liquid, gel, or powder. Since suitable bonding materials may be spread onto the surfaces of the cradle portion 30 and the spinal stabilization element 20 or injected into the cavity 50, suitable bonding materials may have a viscosity that allows for this type of application. For example, suitable bonding materials may have a viscosity between about 50 cps-250,000 cps, or about 1000-2000 cps at room temperature. One example of a commercially available bonding material is a two-component epoxy such as grade EP30MED from Master Bond, Inc. of Hackensack, N.J.

The bonding material 51 may also be curable such as, for example, chemically curable, photo-curable, UV curable, or acoustically curable. The bonding material 51 may have a cure time that provides sufficient bond strength to hold or attach the fastener 13 to the spinal stabilization element 20 within a desired amount of time. For surgical procedures, bonding materials that cure, or set up, in between about 1-60 minutes at room temperature are suitable. However, bonding materials with longer cure times may be suitable as well. For example, if a mechanical fastener or device is used to provide supplemental support or bonding strength, bonding materials with cure times between about 24-48 hours at room temperature may be suitable. In addition, it may be possible to reduce the cure time of suitable bonding materials with heat or energy such as UV light.

Spinal stabilization elements 20, 22 are used to provide a desired spinal function such as spacing or curvature of the vertebra 24, 26 to which they are attached. The spinal stabilization elements 20, 22 may include any suitable spinal stabilization devices or tools. For example, the spinal stabilization elements 20, 22 may include rigid rods and bars. The spinal stabilization elements 20, 22 may also include cords or ropes that have a degree of flexibility and compressibility. One example of a commercially available spinal stabilization element includes the flexible cord used in the Dynesys™ Dynamic Stabilization System, available from Zimmer Spine, Inc. (Minneapolis, Minn.).

Figure 2:
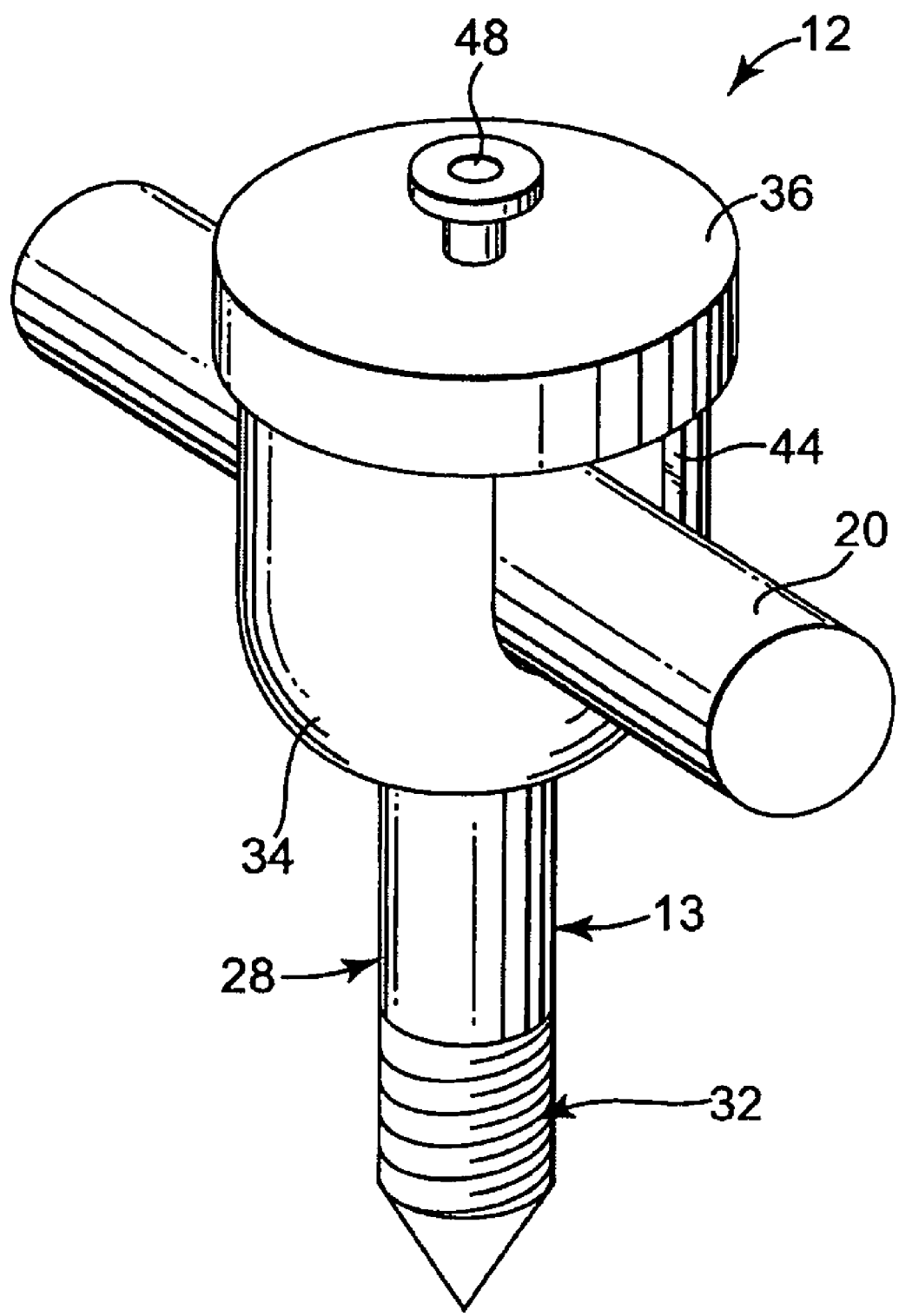
FIG. 2 is a perspective view of one embodiment of an attachment device in accordance with the present invention which includes a fastener for attaching to a vertebra and a spinal stabilization element connected to the fastener.

Any suitable attachment device 12 may be used with the present invention. The spinal stabilization system 10 may use a combination of attachment devices in accordance with the present invention or other developed attachment devices. One example of an attachment device 12 is shown in further detail in FIGS. 2-4. The attachment device 12 may include a fastener 13 that has a connector portion 28 at a distal end that is configured to engage with or be implanted in a vertebra and a cradle portion 30 that is configured to receive a spinal stabilization element 20. The connector portion 28 may include a threaded portion 32 to engage with the bone, as illustrated, or may include a hook portion (not shown) or other bone engaging device known or developed.

The fastener 13 may be formed as a single piece or may be formed from plural pieces that are assembled. In one embodiment, the cradle portion 30 may be provided as an integral portion of the fastener 13, as shown. However, in another embodiment, the cradle portion 30 may be provided as a separate component that is attached to the fastener 13. The fastener 13 may also include any desired mechanical device or element for providing relative movement between the fastener 13 and the spinal stabilization element 20 for adjusting the fastener 13 with respect to the spinal stabilization element 20. For example, the fastener 13 may also include devices for providing linear movement between the fastener 13 and the spinal stabilization element 20 such as for adjusting the length of the fastener 13. The fastener 13 may also include devices for providing rotational or articulating motion between the fastener 13 and the spinal stabilization element 20. For example, a ball joint or similar device that can optionally be rigidly fixed after a desired amount of adjustment through bonding or mechanical securing may be included as a component of the fastener 13.

The cradle portion 30 (FIG. 4) may be positioned at a desired location along the length of the spinal stabilization element 20 for attaching the fastener 13 to the spinal stabilization element 20. Further, the cradle portion 30 of the fastener 13 may be capable of cooperating with the spinal stabilization element 20 for at least partially positioning the spinal stabilization element 20 with respect to the fastener 13. As such, the cradle portion 30 may include a surface portion, such as surface portion 31, that engages with a surface portion, such as surface portion 21, of the spinal stabilization element 20. Such surface portions may be used to help bond the fastener 13 to the spinal stabilization element 20 with one or more bonding materials as described above.

Figure 5:
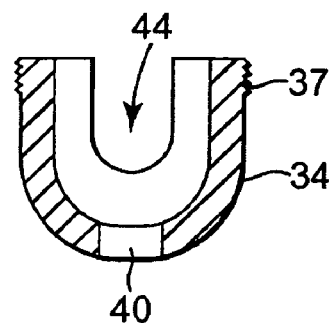
FIG. 5 is a cross-sectional view of the body of the attachment device of FIGS. 2, 3 and 4.

The attachment device 12 also includes a body 34 and a cap 36. As illustrated in FIG. 5, the body 34 may be cup-shaped to define in part an internal space and may include an opening 40 that allows the fastener 13 to pass through the body 34. The cradle portion 30 of the fastener 13 may be maintained within the internal space of the body 34 with the connector portion 28 passing through opening 40 to extend out from the body 34. The lower interior surface of the body 34 may correspond to the external surface of the cradle portion 30 to facilitate positioning and adjustment. In one embodiment, illustrated in FIG. 9, a small clearance 33 exists between the lower interior surface of the body 34 and the external surface of the cradle portion 30 so that they may also be bonded together in a manner as described below. The body 34 may also include side slots 44 diametrically arranged to receive the spinal stabilization element 20. The slots 44 may be shaped at their inner ends to correspond to the spinal stabilization element 20 for fitting and bonding as described above.

The body 34 may be made from any desired material. For example, the body 34 may be made from a semi-crystalline high temperature thermoplastic such as polyetheretherketone ("PEEK") or the like. The body 34 may also be made from metals, ceramics, other plastics and the like as such materials that are suitable for use within the human body. Materials chosen for the body 34 or other components of the present invention may be radio-opaque or radiolucent so as to facilitate the X-ray visibility of the body 34 or other component once implanted within a patient. PEEK thermoplastic material is one example of a suitable radiolucent material.

The body 34 may be made as a single piece or be made from plural pieces that can be assembled by any technique to form the body 34. For example, the body 34 can be formed as a clamshell structure and may include engagement elements for attaching sides of the body 34 to each other. Such engagement elements may include male and female portions that can snap or otherwise be connected together. The body 34 may also include a hinge portion for connecting opposite sides of the body 34. If the body 34 is formed from plural pieces, such pieces can be attached to each other with an adhesive, mechanical securement, welding or similar mechanisms.

The cap 36 may include internal threads 35 to connect with threads 37 of the body 34 so that the cap 36 can be adjustably attached to the body 34 and tightened against the spinal stabilization element 20. An edge surface 27 of the cap 36 may engage the spinal stabilization element 20 as in known retaining nuts. The cap 36 may also include at least one port or inlet 48 for supplying bonding material for bonding the fastener 13 to the spinal stabilization element 20 as described above. Alternatively, the inlet 48 may be provided through the body 34 or through both the cap 36 and body 34. The inlets 48 may be provided in any manner. For example, the inlet 48 may include a nipple as shown or may include any opening or port of any design. In one embodiment, the inlet 48 is able to engage with a delivery device that includes or is operationally connected to a supply reservoir for supplying bonding material to the cavity 50. If desired, the inlet 48 may include a one-way valve such as a check valve or a flow regulating valve. The inlet 48 may also include any seal or membrane that may need to be punctured, cut or removed as part of the supply process.

As illustrated in FIG. 4, the fastener 13 may be positioned partially within the body 34 so that the fastener 13 passes through the opening 40 and the cradle portion 30 of the fastener 13 rests against the internal wall of the body portion 34. The cradle portion 30 of the fastener 13 may rest against the body portion 34 so that the fastener 13 may move to a predetermined degree with respect to the body 34 for adjusting the relative position of the fastener 13 and the spinal stabilization element 20. For example, the fastener 13 and the cradle portion 34 may rotate with respect to a direction of extension of the spinal stabilization element 20, such as an axis extending along the length of the spinal stabilization element 20. The cradle portion 30 may allow for polyaxial adjustment between the fastener 13 and the spinal stabilization element 20. For example, using rounded surfaces on the external surface of the cradle portion 30 and the internal surface of the body 34, as shown, the cradle portion 30 may rotate and be angularly adjustable to the extent permitted by the size of opening 40. Opening 40 may be tapered or slotted to facilitate greater movement in any desired direction while holding the cradle portion 30 in position. A sufficient space 33 may be provided between the cradle portion 30 and body 34 to facilitate a desired degree of movement. Otherwise, the cradle portion 30 may include any known or developed ball joint or other mechanical device, including any number of components, for providing polyaxial movement. For only rotation, the cradle portion 30 and body 34 may be non-rounded to prevent angular movement.

In one embodiment, illustrated in FIGS. 4-6, the cap 36 is connected to the body 34 by threading the cap 36 onto an external edge portion of the body 34. In this embodiment, the body 34 includes threads 37 on an external edge portion while the cap 36 includes internal threads 35, as illustrated in FIGS. 5 and 6. In another embodiment, described in greater detail below and illustrated in FIGS. 7 and 8, the cap 136 includes external threads 135 thread with the internal threads 137 on an internal edge portion of the body 134.

By threading the cap 36 onto the body 34, the surface 27 of the cap 36 can be driven hold the spinal stabilization element 20, as shown in FIG. 3. The spinal stabilization element 20 can thus be driven into the cradle portion 30 of the fastener 13 and the cradle portion 30 can be driven against the body 34. As such, the fastener 13 can be held in place with respect to the spinal stabilization element 20 and further attached to the spinal stabilization element 20 with bonding material 51. In one embodiment, the cap 36 may be used to provisionally hold the fastener 13 with respect to the spinal stabilization element 20. That is, the cap 36 may be tightened to a desired holding force sufficient to hold the construct at least temporarily while the bonding material is applied to attach the spinal stabilization element 20 to the fastener 13. In another embodiment, the force provided by the cap 36 is utilized to stabilize the system along with the bonding force.

Procedures or methods of using such attachment devices with one or more spinal stabilization elements to create a spinal stabilization construct are described as follows. These steps may be conducted as often or in any order as desired to create a spinal stabilization system in accordance with the present invention.

In one method of the present invention, the fastener 13 is inserted through the opening 40 of the body 34 such that the cradle portion 30 engages with the body 34. If the fastener 13 includes a bone engaging portion such as a bone hook that cannot be inserted through 10 the opening 40, the fastener 13 may be formed as plural pieces or the body 34 may be formed as plural pieces so that the fastener 13 and the body 34 may be assembled with respect to each other and in accordance with the present invention. In other words, a portion of the fastener 13 on one side of the opening 40 may be attached to a portion of the fastener 13 on the opposite side of the opening 40, such as by using threaded connections, other mechanical fasteners, bonding or welding techniques, or other known or developed connection methods.

Next, the fastener 13 is implanted in or engaged with a vertebra in any conventionally known or developed manner. Accordingly, where the fastener 13 includes a bone screw, the fastener 13 may include an engaging portion for driving the fastener 13. For example, as shown in FIGS. 4 and 9, the fastener 13 may include a socket 52 for implanting the fastener 13 into the vertebra by engaging the socket 52 with a wrench or other driving tool or the like. Any cooperating engagement arrangement for driving such a screw is contemplated. The fastener 13 may be partially or fully implanted in a vertebra before the body 34 is assembled around the fastener 13

After the fastener 13 is implanted or otherwise secured in place to a vertebra, a spinal stabilization element 20 may be positioned to extend through the slots 44 followed by threading the cap 36 into engagement with the spinal stabilization element 20. At least a temporary stabilization of the spinal stabilization element 20 and fastener 13 may be created by sufficiently tightening the cap 36 in place. The cap 36 may be driven so that the spinal stabilization element 20 seats in the cradle portion 30 and is held in place by the cap 36. At this point, bonding material 51 may be introduced or injected through the inlet 48 to provide bonding material 51 in the cavity 50. The bonding material may be cured in any desired manner and for any length of time to provide a sufficient bond between the fastener 13 and the spinal stabilization element 20.

Alternatively, bonding material 51 may be supplied before the spinal stabilization element 20 is seated in the cradle portion 30 so that at least one of the mating surfaces of the spinal stabilization element 20 and the cradle portion 30 are coated with bonding material 51. The cap 36 can then be used to seat the spinal stabilization element 20 within the cradle 30 by using the cap 36 to press the spinal stabilization element 20 into the cradle 30 and to permit the surface portions to bond together sufficiently.

Figure 10:
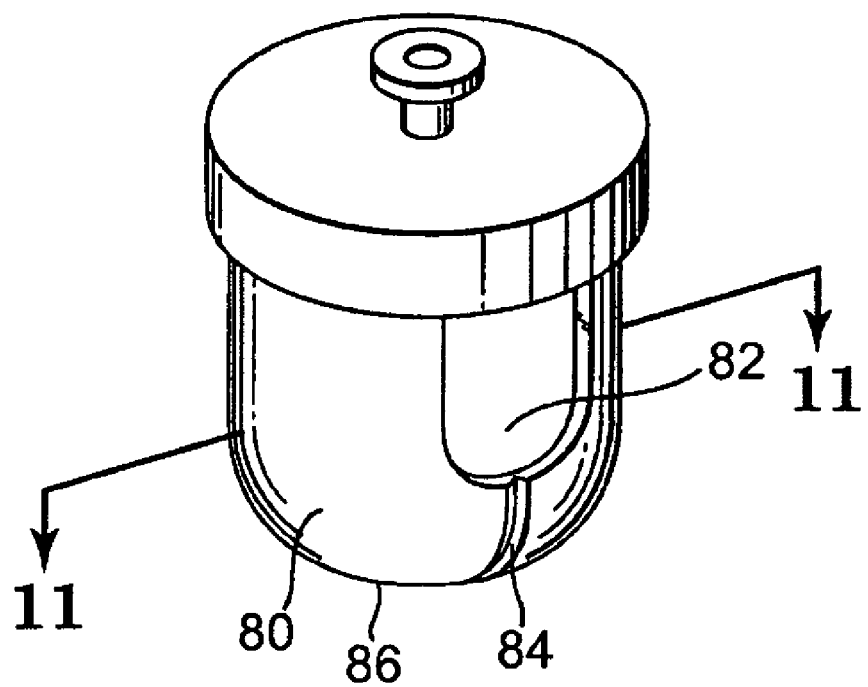
FIG. 10 is a perspective view of an alternative embodiment of a body with a notch that may be used to remove the body and a cap, each in accordance with the present invention.
Figure 11:
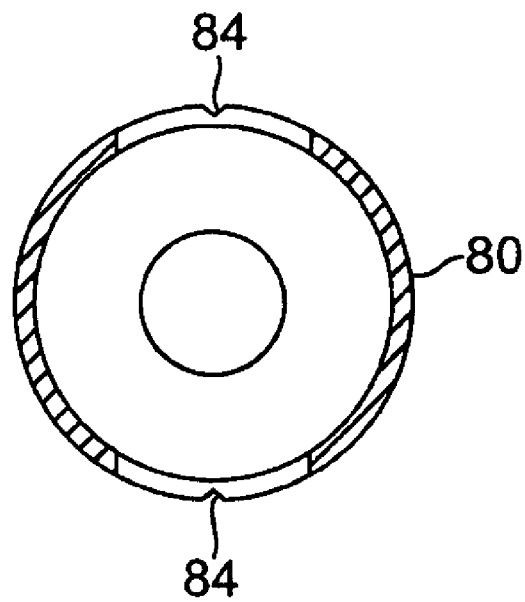
FIG. 11 is a cross-sectional view of the body of FIG. 10 taken along the line 11-11.

In one embodiment, the body 34 and cap 36 are not removed after the bonding material sufficiently cures and attaches the fastener 13 to at least a surface portion 21 of the spinal stabilization element 20. In another embodiment, the body 34 and cap 36 may be removed after the bonding material has cured to form a bond having a desired strength. In this embodiment, the body 34 may include one or more features to facilitate removal of the body 34 from the bonding material 51. For example, as illustrated in FIGS. 10 and 11, a body 80 may include notches 84 that extend from a low point of the slot 82 to an edge of the body 86 on opposite sides of the body 80. The notches 84 may provide a thinned portion of the wall of the body 80 that can be controllably fractured to remove the body 80. Removal of the body 80 from the remaining fixed construct may also be facilitated by its having been assembled from plural pieces. Also, the body 80 may include relief features such as drafts or tapers or the like to facilitate removal of the body 80 from the bonding material. Alternatively, the material used to form the body 80 or the bonding material may be chosen or treated to control adhesion of the bonding material to the body 80 so that the body 80 can be easily removed from the bonding material. This step of removing the body may be suitable, for example, to provide a more flexible bond between the spinal stabilization element and the fastener.

Figure 8:
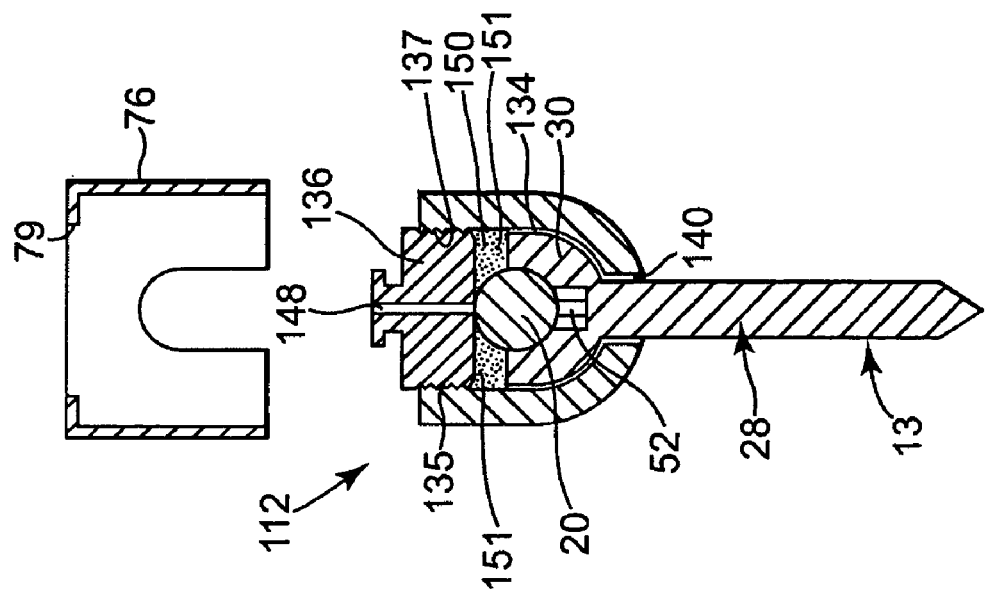
FIG. 8 is a cross-sectional view of the attachment device of FIG. 7.
Figure 7:
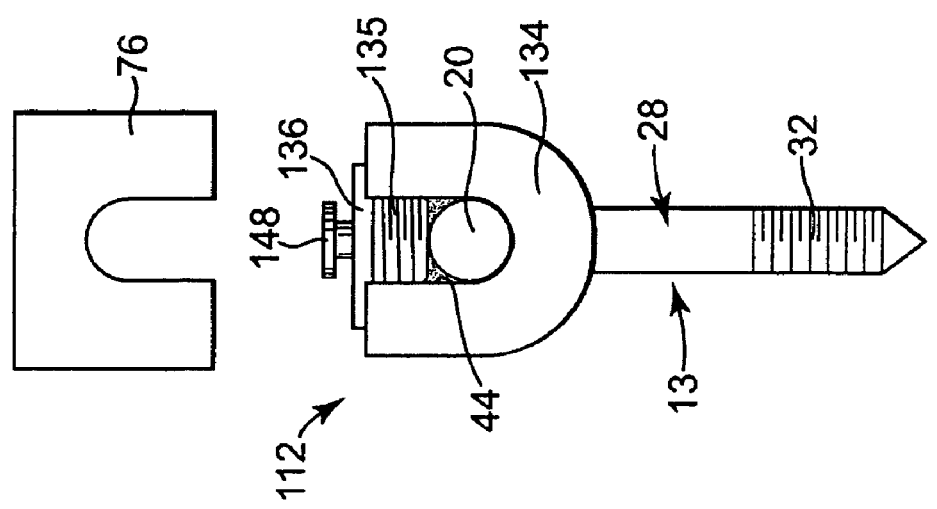
FIG. 7 is side view of another embodiment of an attachment device in accordance with the present invention which includes a fastener connected to a spinal stabilization element, a body, a cap and a cover.

Another embodiment of the spinal stabilization system in accordance with the present invention is illustrated in FIGS. 7 and 8. FIG. 7 illustrates an attachment device 112 with a fastener 13 connected to a spinal stabilization element 20. FIG. 8 illustrates a cross-section of the attachment device 112 and spinal stabilization element 20 shown in FIG. 7. As with the attachment device 12 described above, the attachment device 112 can be used to secure the fastener 13 to the spinal stabilization element 20. As shown, the attachment device 112 includes a body 134 that is generally cup-shaped like body 34 described above and has an opening 140. The body 34 also includes a pair of slots 44, in the same manner as described above, for receiving the spinal stabilization element 20. The fastener 13 may pass through the opening 140 so that the cradle portion 30 of the fastener 13 may seat in the body 134 as illustrated or in any of the manners described or suggested above.

The attachment device 112 also includes a plug-like cap 136 that may be threadingly connected to the body 134 via an internal thread 135 on the body 134 and an external thread 137 on the cap 136, as illustrated. Thus, the cradle portion 30, the body 134, and the cap 136 may cooperatively define a cavity 150 that can receive bonding material 151 for securing the fastener 13 to the spinal stabilization element 20. The cap 136 may include an inlet 148 through which the bonding material 151 may be applied to the cavity 150. The cap 136 may also be used to provisionally hold the spinal stabilization element 20 in an attachment position with respect to the fastener 13 while bonding material 151 is used to further secure the spinal stabilization element 20 to the fastener 13. That is, the cap 136 may function in a manner similar to the cap 36, as described above, for driving the spinal stabilization element 20 into the cradle portion 30.

Also illustrated in FIGS. 7, 8, 17 and 18 is an adhesive containment cover 76, 176 that may be used with the present invention. The adhesive containment cover 76, 176 may substantially surround the spinal stabilization element 20 so that when the cover 76, 176 is positioned on the attachment device 112, the body 34, cap 136 and the cover 76, 176 define a substantially closed internal cavity 150 for receiving the bonding material 151. As such, escape of bonding material 151 from the cavity 150 is limited and may be substantially eliminated.

In one embodiment, illustrated in FIGS. 7 and 8, the cover 76 fits over and around the cap 136 and extends over at least some of the body 134 to block the flow of bonding material 151 from the space left between the slots 44 and the cap 136. An opening 79 permits access to the inlet 148 on the cap 136. The cover 76 may be removed either after the bonding material 151 is supplied into the cavity 150 or after the bonding material 151 is at least partially set or cured, although the cover 76 may stay in place. Material composition of the cover 76 may be chosen to facilitate easy separation from the bonding material 151.

Figure 17:
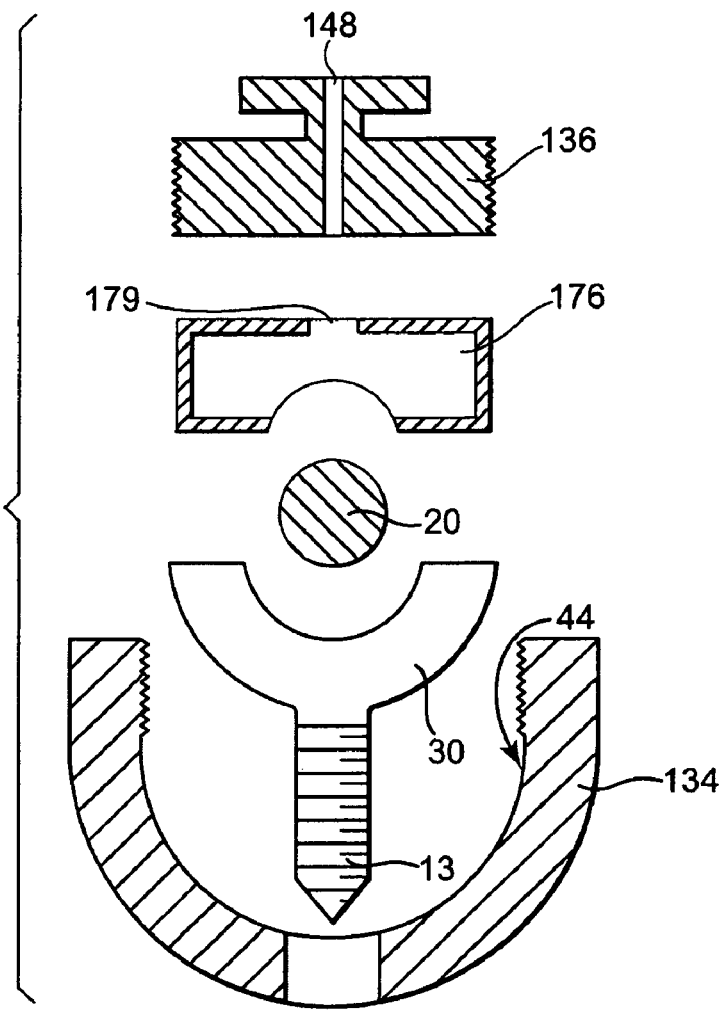
FIG. 17 is an exploded view partially in cross-section of an attachment device in accordance with the present invention which includes a fastener connected to a spinal stabilization element, a body, a cap and a cover.
Figure 18:
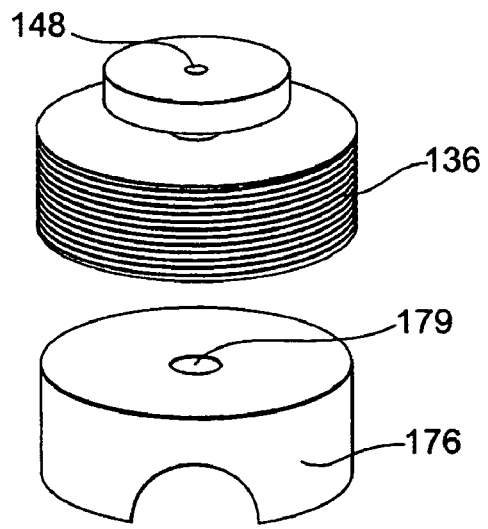
FIG. 18 is a side view of the cap and the cover of FIG. 17.

In another embodiment, illustrated in FIGS. 17 and 18, the cover 176 is positioned between the cap 136 and the fastener 13 to block the flow of bonding material from the space between the slots 44 and the cap 136. The cover 176 may include an opening 179 to permit access from the inlet 148 to the cavity (not shown). The cover 176 may be configured so that a curved or angled portion of the cover 176 can conform to the shape of the spinal stabilization element 20 when positioned on the fastener 13. By fitting the cover 176 with the spinal stabilization element 20, the element 20 may be more effectively held and clamped between the cap 164 and the cradle portion 30 fastener 13. The cover 176 may be independent from the cap 136, as shown, or it may be moveably attached to the cap 136. If the cap 136 is threadingly attached to the body 134, a moveably attached cover 176 may allow the cover 176 to remain engaged with the spinal stabilization element 20 while the cap 136 continues threading onto the body 134.

Figure 14:
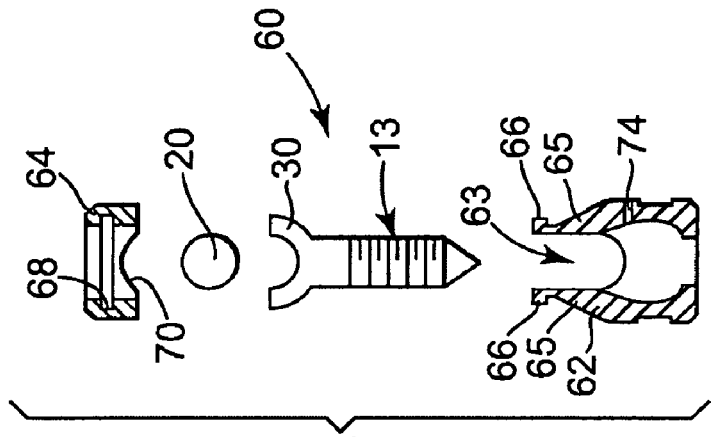
FIG. 14 is an exploded view partially in cross-section of the attachment device of FIGS. 12 and 13.
Figure 13:
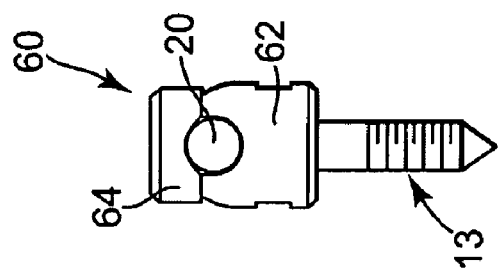
FIG. 13 is a side view of the attachment device of FIG. 12.
Figure 12:
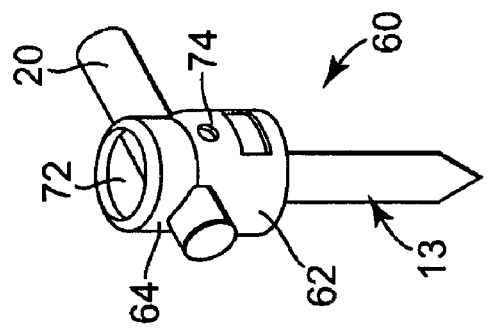
FIG. 12 is a perspective view of still another embodiment of an attachment device in accordance with the present invention which includes fastener connected to a spinal stabilization element, a body, and a cap.

Still another embodiment of the spinal stabilization system in accordance with the present invention is illustrated in FIGS. 12-14. In this embodiment. the body 62 includes slots 63 defining a pair of resiliently deflectable spaced legs 65. Each body includes a lip 66 that is able to engage within an annular channel 68 on the cap 64 when the cap 64 is positioned on the body 62. In this embodiment, the lips 66 cooperate with channel 68 to allow the cap 64 to be snapped onto the body 62. The cap 64 may be removable or not, such as by the engagement between the lips 66 and the channel 68. By using such a snap-on cap 64 and body 62, the application of torque to the attachment location of a spinal stabilization system may be avoided. The body 62 and cap 64 may be used effectively to provide a cavity for the bonding material and may also provide a sufficient clamping or holding force for at least temporarily holding the fastener 13 in a position with respect to the spinal stabilization element 20.

Further referring to FIG. 14, the cap 64 may include a surface portion 70 that is shaped for engagement with the spinal stabilization element 20. As shown, the surface portion 70 may be shaped so that a curved or angled portion of the surface portion 70 can conform to the shape of the spinal stabilization element 20. By fitting the surface portion 70 with the spinal stabilization element 20, the element 20 may be more effectively held and clamped between the cap 64 and the cradle portion 30 of the spinal stabilization element 20. The cap 64 with surface portion 70 may also function to block the flow of bonding material 51 from the space left between the slots and the cap like the cover 76, 176 described above.

Figure 15:
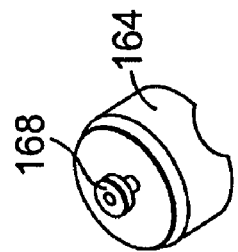
FIG. 15 is a perspective view of one embodiment of a cap in accordance with the present invention which includes an inlet for supplying bonding material to the interior of the body.

As shown in FIG. 12, the cap 64 may also include an inlet 72 that may be used to introduce bonding material into the body 62 for further securing the fastener 13 to the spinal stabilization element 20. However, it is contemplated that the cap 64 may be closed, if desired. The body 62 may suitably include an inlet 74, as shown, that can be used to introduce bonding material into the body 62 instead of or in addition to any inlet of the cap 64. As above, inlets may include any type of port, nipple or other suitable device that facilitates introduction of bonding material into the cavity. For example, as shown in FIG. 15, another embodiment of the cap 164 is shown that includes an inlet 168 that functions in the same manner as the inlets 48 and 148 described above to introduce bonding material through the cap 164. As above, bonding material can be introduced into the construct before the cap 164 is put in place.

Figure 16:
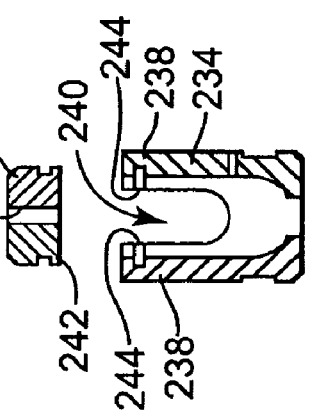
FIG. 16 is a cross-sectional side view of another embodiment of a body and cap in accordance with the present invention.

Yet another embodiment of the cap 236 and the body 234 is illustrated in FIG. 16. In this embodiment, the cap 236 may snap-fit with an internal edge portion of the body 234. The body 234 includes leg portions 238 that are defined by slots 240 (only one shown) and that are resiliently deformable to permit a flange portion 242 of the cap 236 to fit within inside grooves 244 provided along the internal edge portions of the legs 238. As above, the cap 236 can be removable from the body 234 after the snap-on connection, or not. Either the body 234 or the cap 236 may include an inlet, such as inlet 246 through the cap 236, to permit application of bonding material within the interior space of the body 234 when closed by the cap 236 for supporting a spinal stabilization element in a similar manner as described above.

The present invention has now been described with reference to several embodiments thereof. The entire disclosure of any patent or patent application identified herein is hereby incorporated by reference. The foregoing detailed description and figures have been given for clarity of understanding only. No unnecessary limitations are to be understood from the detailed description and figures. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A system for use in spinal stabilization comprising:
   a fastener comprising a cradle portion having a concave upper surface defining a recess extending longitudinally along a longitudinal axis from a first side of the cradle portion to a second side of the cradle portion, and a connector portion extending from the cradle portion;
   an elongate spinal stabilization element positioned in the recess of the cradle portion such that the elongate spinal stabilization element extends generally parallel to the longitudinal axis such that a convex surface of the elongate spinal stabilization element rests against the concave upper surface of the cradle portion at a desired location;
   a body movably disposed to the cradle portion of the fastener; and
   a cap connected to the body, wherein the concave upper surface of the cradle portion, an interior surface of the body, and the cap define a cavity that at least partially surrounds a surface of the spinal stabilization element;
   wherein at least one of the body and the cap comprises an inlet;
   wherein the inlet comprises a valve.

2. The system of claim 1, wherein the cap connects to an internal edge portion of the body.

3. The system of claim 2, wherein the cap comprises external threads and the internal edge portion of the body comprises internal threads.

4. The system of claim 1, wherein the body comprises a radiolucent material.

5. The system of claim 1, further comprising a cover removably attached to the body.

6. The system of claim 1, further comprising a cover removably attached to the cap.

7. The system of claim 1, wherein the body comprises notches.

8. The system of claim 1, further comprising bonding material configured to be disposed within the cavity to bond a portion of the fastener to a portion of the spinal stabilization element.

9. The system of claim 8, further comprising a clearance between the body and the cradle configured to receive bonding material.

10. The system of claim 1, further comprising bonding material configured to be injected into the cavity through the inlet, the bonding material configured to bond a portion of the fastener to a portion of the spinal stabilization element.

11. A system for using in spinal stabilization comprising:
    a spinal stabilization element;
    a body including a cavity defined therein, first and second side slots diametrically arranged on opposite sides of the body and opening into the cavity, and an opening extending through a base portion of the body, wherein the first and second side slots are arranged to receive the spinal stabilization element through the cavity of the body;
    a fastener coupled to the body, wherein a threaded connector portion of the fastener extends through the opening of the body;
    a cap removably coupled to the body;
    a quantity of bonding material configured to bond the spinal stabilization element to the body, the bonding material disposed within the cavity and contacting a portion of the spinal stabilization element extending through the cavity and the body;
    wherein at least one of the body and the cap includes an inlet for injecting the bonding material into the cavity;
    wherein the inlet includes a one-way valve preventing bonding material from exiting out through the inlet.

* * * * *